Nov. 12, 1963 O. O. DUNHAM Plant Pat. 2,297
CHRYSANTHEMUM PLANT
Filed April 2, 1962
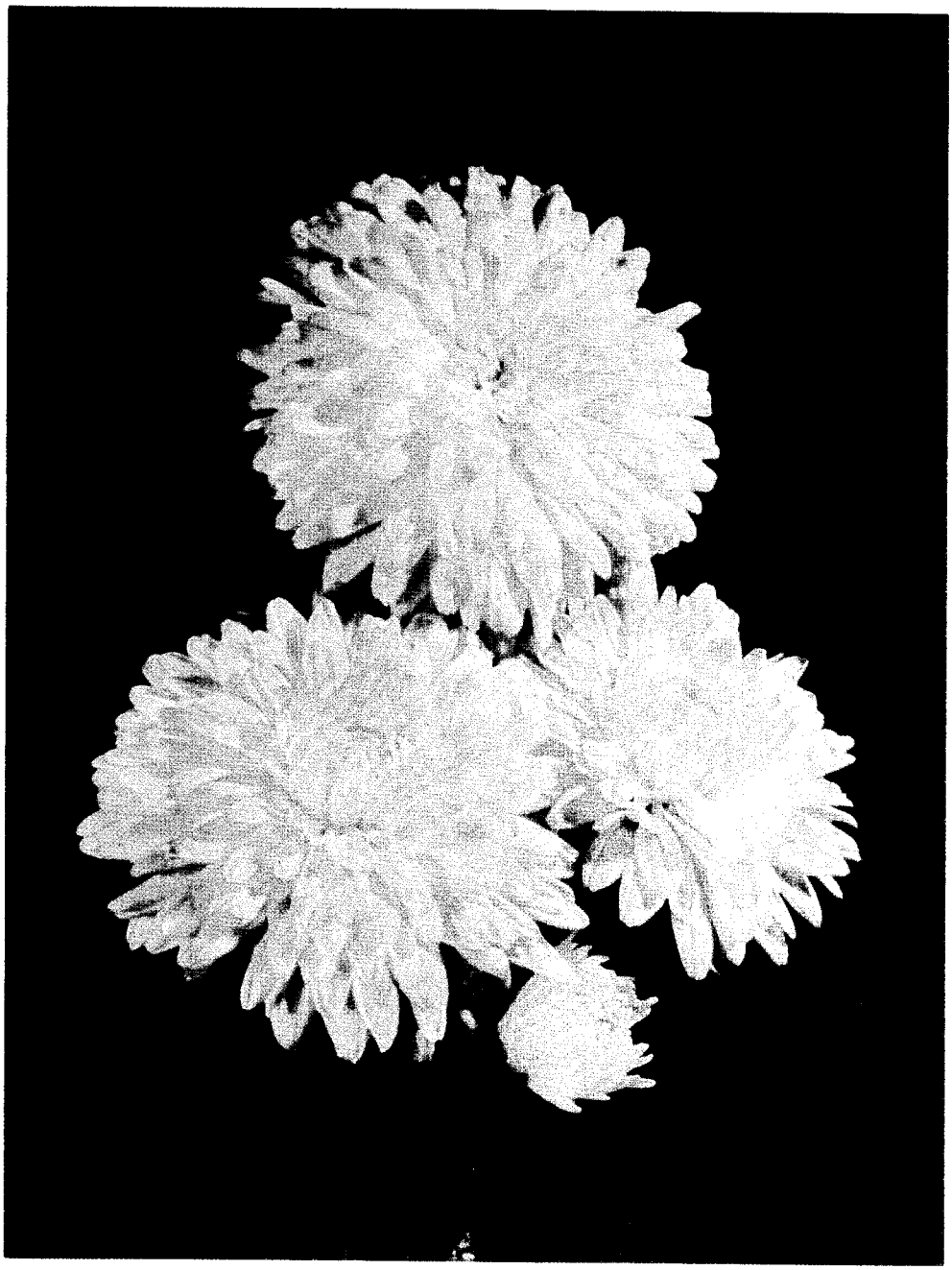
Inventor:
O. O. DUNHAM
by Robb & Robb
attorneys United States Patent Office Plant Pat. 2,297
Patented Nov. 12, 1963

2,297
CHRYSANTHEMUM PLANT

Orville O. Dunham, Rte. 4, Niles, Mich.

Filed Apr. 2, 1962, Ser. No. 184,614
1 Claim. (Cl. Plt.—77)

My present invention comprises a new and distinct variety of chrysanthemum plant, developed by crossing the variety "Nanook," an unpatented variety, with another unpatented variety known as "Cameo."

The object of this invention is to produce a new variety of chrysanthemum which is superior to either parent, the chrysanthemum being of the *indicum* type and deriving certain attributes, including the color and early blooming habit from one parent and the better plant habit from the other, the more profuse blooming resulting for each plant being apparently a combination and better than either of the parents. The plant itself is more compact and develops more foliage than either of the parents likewise.

The present new variety of chrysanthemum is the result of a careful program of development and analysis of the characteristics, this new variety being an example of the ability to select carefully and cross breed for particular advantage from various parent plants to derive characteristics of each which are good and the combination which is better than the general strain from which the said parents have derived, early flowering and continuous flowering being desirable in this particular field as is well known.

As a result of the specific hybridization previously mentioned my present new and distinct variety of chrysanthemum has been produced and is characterized by the brilliant yellow to creamy white color of its blooms which are developed in clusters, on strong short stems, the blooms retaining their form and the petals being very double.

More specifically the blooms of my new variety are of a brilliant yellow to creamy white color (Nickerson Color Fan published by The Munsell Color Company), the center being the yellow referred to and the petals becoming lighter as they are spaced from the center. As grown in the vicinity of Niles, Michigan, under uniform culture, plants of this variety are grown to an average height of 12" to 14" with a large quantity of blooms creating a cluster in most cases.

My new variety obtains a number of characteristics from both parents but actually includes a much better plant habit, being more compact and having more foliage, this likewise differing from both of the parents and from other known varieties.

My new variety when grown in the region of Niles, Michigan, is a very profuse blooming plant from mid-September until a killing frost, the blooms being small and compact in clusters on each plant.

My new variety has been asexually reproduced by cuttings in the vicinity of Niles, Michigan, and said new variety has been found to retain its distinctive characteristics through successive asexual reproduction.

The accompanying drawing forming a part hereof shows a typical plant of my new variety of chrysanthemum.

The following is a detailed description of my new variety of chrysanthemum plant, the color references being to the Nickerson Color Fan published by The Munsell Color Company:

*Description*

Parentage: Seedling.
- *Seed parent.*—"Nanook" (unpatented).
- *Pollen parent.*—"Cameo" (unpatented).

Classification: Botanic—*Chrysanthemum indicum.*

*Flower*

Blooming habit: Blooms continuously and profusely from mid-September until a killing frost. Observations were made in the vicinity of Niles, Michigan during September and October.

Bud:
- *Size.*—Small.
- *Form.*—Short with flat top.
- The bud is not affected by wet or hot weather.

Color:
- *When petals begin to unfurl.*—2.5Y 9/9.
- *When half blown.*—Inside of petals—5Y 9/9. Reverse of petals—5Y 9/9.
- *Calyx.* — Shape — funnel. Size — small. Aspect — hairy.
- *Peduncle.* — Length — medium. Aspect — rough. Strength—stiff and erect. Bud opens well and is not affected by adverse weather conditions.

Bloom:
- *Size.*—Small. Average size when fully expanded—2"
- *Borne.*—In clusters and irregular.
- *Stems.*—Short, strong.
- *Form.*—When first open—flat. Permanence—retains its form to the end.
- *Petalage.*—Very double, many petals and stamens hidden. Innumerable petals under normal conditions.
- *Color.*—Center of flower—5Y 9/9. Outer petals—white. Base of petals (singlet)—creamy white. Inside of petals—white. Reverse of petals—white. General tonality from a distance—creamy white.
- *Discoloration.*—General tonality at end of: First week—retains same color. Second week—retains much the same color. Third week—retains much the same color.

Petals:
- *Texture.*—Thin; not affected by hot or wet weather.
- *Appearance.*—Inside—velvety. Outside—satiny.
- *Form.*—Oval.
- *Arrangement.*—Imbricated.
- *Persistence.*—Hang on and dry.
- *Fragrance.*—None.
- *Lastingness.*—On the plant—very long. Cut flower—long.

Genital organs:
- *Stamens, anthers.*—Small, few.
- *Arrangement.*—Regular around styles.
- *Styles.*—Columnar.
- *Ovaries.*—All enclosed in calyx.

Fruit: Variety is fertile with its own pollen.
- *Form.*—Oblong shaped.
- *Aspect.*—Rough.

Plant:
- *Form.*—Bush.

*Growth.*—Vigorous, dwarf and branching.

Foliage:

*Size.*—Medium.

*Quantity.*—Abundant.

*Shape.*—3 lobed.

*Texture.*—Upper side—velvety and flat. Under side—smooth.

*Stipules.*—Short.

I claim:

A new and distinct variety of chrysanthemum plant substantially as herein disclosed, characterized as to novelty by the brilliant yellow center to creamy white outer petal color of its blooms, the profuse and greater weather resistance thereof, the more numerous foliage, the better habit, greater substance, and more compact shape of the plant and better, earlier, more weather and frost resistant nature thereof.

No references cited.